(12) United States Patent
Kimble et al.

(10) Patent No.: US 6,833,489 B1
(45) Date of Patent: Dec. 21, 2004

(54) ASSAYS FOR MODULATORS OF PROLYL-4-HYDROXYLASE

(75) Inventors: Judith E. Kimble, Madison, WI (US);
Ronald T. Raines, Madison, WI (US);
Lisa C. Friedman, Richmond (CA)

(73) Assignee: Wisconsin Alumni Research Foundation, Madison, WI (US)

( * ) Notice: Subject to any disclaimer, the term of this patent is extended or adjusted under 35 U.S.C. 154(b) by 178 days.

(21) Appl. No.: 09/663,805

(22) Filed: Sep. 15, 2000

Related U.S. Application Data
(60) Provisional application No. 60/154,267, filed on Sep. 16, 1999.

(51) Int. Cl.[7] .................. G01N 33/00; A01K 67/00; A01K 67/33
(52) U.S. Cl. .................. 800/3; 800/13; 800/8
(58) Field of Search .................. 800/3, 8, 13; 435/455, 435/441, 448

(56) References Cited

PUBLICATIONS

Levy et al. Molecular and genetic analyses of the caenorhabditis elegans dpy–2 and dpy–10 collagen genes. A variety of molecular alterations affect organismal morphology pp. 803–817 vol. 4 1993.*

Hill et al. dpy–18 Encodes an a–subunit of proly–4–hydroxylase in caenorhabditis elegans pp 1139–1148 2000.*

M. Bickel, et al., "Selective Inhibition of Hepatic Collagen Accumulation in Experimental Liver Fibrosis in Rats by a New Prolyl 4–Hydroxylase Inhibitor," *Heptology* pp. 403–404, 1998.

L. Friedman, et al., "Prolyl 4–Hydroxylase is Required for Viability and Morphogenesis in *Caenorhabditis elegans*," *Proc. Natl. Acad. Sci. USA* 97 (9):4736–4741, 2000.

V. Gunzler and K, Weidman, "Prolyl 4–Hydroxylase Inhibitors," *Prolyl Hydroxylase, Protein Disulfide Isomerase, and Other Structually, Related Proteins*, pp. 65–95, 1997.

N.A. Guzman, "Prolyl 4–Hydroxylase: An Overview," *Prolyl Hydroxylase, Protein Disulfide Isomerase, and Other Structurally Related Proteins*, pp. 1–64–1997.

J. Veijola, et al., "Cloning Baculovirus Expression , and Characterization of the α Subunit of Prolyl 4–Hydroxylase from the Nematode *Caenorhabditis elegans*," *J. Biol. Chem.* 269(43):26746–26753, 1994.

* cited by examiner

Primary Examiner—Ram R. Shukla
(74) Attorney, Agent, or Firm—Quarles & Brady LLP

(57) ABSTRACT

A method for evaluating a test compound's ability to modulate prolyl 4-hydroxylase is disclosed. In one embodiment, the method comprises the steps of introducing a test compound into a test chimeric, P4H-gene modified, or a wild-type nematode, wherein the test chimeric nematode has a complemented prolyl-4-hydroxylase gene mutation, and observing the effect of the test compound on the prolyl 4-hydroxylase activity of the progeny of the test chimeric, P4H-gene modified, or the wild-type nematode, wherein a dpy or embryonic lethal phenotype indicates prolyl-4-hydroxylase inhibition.

14 Claims, 3 Drawing Sheets

Inhibitor I

Inhibitor II

Inhibitor III

Inhibitor IV

ASSAYS FOR MODULATORS OF PROLYL-4-HYDROXYLASE

CROSS-REFERENCE TO RELATED APPLICATION

This application claims priority to U.S. provisional application Ser. No. 60/154,267, filed Sep. 16, 1999. Ser. No. 60/154,267 is incorporated by reference as if fully set forth herein.

This invention was made with United States government support awarded to the following agency: NIH AR44276. The United States has certain rights in this invention.

STATEMENT REGARDING FEDERALLY SPONSORED RESEARCH OR DEVELOPMENT

BACKGROUND OF THE INVENTION

Prolyl-4-hydroxylases (P4H) are enzymes that modify collagen in a manner that stabilizes the conformation of collagen. The synthesis of hydroxyproline residues by P4H is a critical step in intracellular collagen processing.

Reduced P4H enzyme activity leads to unstable collagen and disease symptoms such as those seen in patients suffering from scurvy. Increased activity creates less pliable tissue and is associated with fibrotic diseases. P4H is recognized as an ideal target for the pharmacological control of collagen biosynthesis (Bickel, et al., *Hepatology* August:404–405, 1998).

BRIEF SUMMARY OF THE INVENTION

We have discovered an assay for modulators of P4H enzyme activity in the nematode *Caenorhabditis elegans*. Loss of one isoform of prolyl-4-hydroxylase causes the nematode to be short and fat, a morphology termed "dumpy" or "dpy". (There are other nematode genes that can be mutated to the dpy phenotype, but there are methods known to one of skill in the art for determining which gene is responsible for the phenotype.) Loss of the second isoform of prolyl4-hydroxylase while retaining the first isoform of prolyl4-hydroxylase gives the nematode no apparent phenotype. Mutations in both prolyl-4-hydroxylase isoforms in the same animal result in embryonic lethality. The embryos develop to the pretzel stage and then retract into a mass of cells. These phenotypes provide an easy assay for detecting changes in prolyl4-hydroxylase activity.

In another embodiment of the present invention, one would introduce the human version of P4H-gene into a P4H-modified nematode and, thus, complement the P4H mutation. One would then expose the test chimeric nematode to a test compound and determine whether the test compound interferes with the P4H activity by examining whether the chimeric nematode or its progeny develop a phenotype that can be attributed to modified P4H activity. We predict that the P4H-modified nematode, which has been exposed to the test compound, will have a phenotype similar to the dpy-18 mutant or the phy-1 mutant or the combined dpy-18; phy-1 double mutant phenotype.

In another embodiment of the present invention, one would attempt to recover P4H activity, thus indicating that the test compound is a P4H activator. In that embodiment, one would introduce a test compound to a P4H-modified nematode and examine the nematode and its progeny for either recovered P4H activity or a phenotype demonstrating wild-type P4H activity.

DETAILED DESCRIPTION OF THE INVENTION

Figure 1:
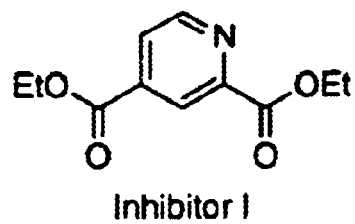
FIG. 1 diagrams four different putative prolyl 4-hydroxylase inhibitors.
Figure 1:
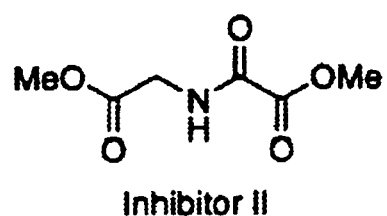
Figure 1:
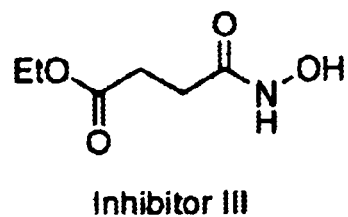
Figure 1:
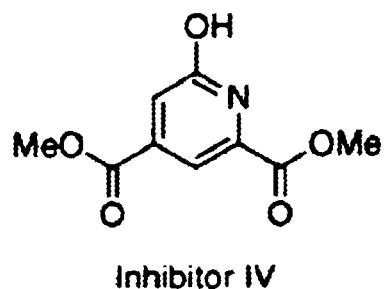

In one embodiment, the present invention is a system designed to look for modifiers (inhibitors and activators) of prolyl 4-hydroxylase activity.

Inhibitors that specifically target human prolyl 4-hydroxylase alpha subunits (I or II) could be used to help people suffering from fibrotic diseases. Activators that specifically target the human prolyl 4-hydroxylase could be used to help treat diseases with Scurvy-like symptoms (underhydroxylated collagen or unstable collagens). Inhibitors or activators that specifically target any protein or molecule with prolyl 4-hydroxylase activity which can function in place of the dpy-18 gene in the transgenic assay could be used as nematode or drosophila pesticides.

In a preferred embodiment, the assay would take place as follows:

Test nematodes will be exposed to a test compound to assay the effect of the compound on prolyl 4-hydroxylase activity. Suitable test nematodes used will include dpy-18 animal rescued by the human alpha I subunit of prolyl 4-hydroxylase, dpy-18 animal rescued by the human alpha II subunit of prolyl 4-hydroxylase, wild type *C. elegans*, dpy-18 mutants, phy-2 mutants and various dpy-18; phy-1 mutant combinations. We have included some of these test nematodes to screen for inhibitors of nematode P4H which could potentially be used as pesticides. Combinations of mutant phenotypes could be used to look for specific gene inhibition and potentially specific gene activation. (The Examples below describe the isolation and characterization of the mutants. In general dpy-18 is a deletion isolated specifically as a knock-out of the P4H gene on chromosome III and PHY-2 is a deletion mutant isolated specifically as a knock-out of the P4H gene on chromosome IV.)

In the methods of the present invention, one may wish to use particular test nematodes with modified P4H activities. Friedman, et al. (*Proc. Natl. Acad. Sci. USA* 97(9): 4736–4741, 2000, incorporated by reference as if fully set forth herein) describes the creation of mutants useful for the present invention. Particularly, Friedman, et al., 2000 describes the creation of dpy-18 and phy-2 mutations. In general, we refer to these mutations as "P4H-gene modified nematodes." We refer to the P4H-gene modified nematodes that have been rescued with a human P4H gene as "test chimeric nematodes" or "test chimeric *C. elegans*."

In one embodiment, the test chimeric nematodes or wild-type nematodes will be exposed to test compounds such as chemicals, gene products, and natural products, by various different methods. Preferably, the nematodes will be placed in a solution containing the test compound and soaked for a period of time, or the test compound may be placed directly in the growth medium or on a slide, or introduced through a hole in the egg shell or introduced into the animal by injection into the germline. A suitable length of time would be determined experimentally based on the compound of interest and the age at which one would like to expose the worm.

In one embodiment, the test compound is part of a combinatorial chemical library.

If the test compound is an inhibitor of prolyl4-hydroxylase activity, we expect the nematode's progeny to appear dpy or die, depending on whether the inhibitor is gene-specific or knocks out both prolyl-4-hydroxylase genes. For example, if the inhibitor is gene-specific to the DPY-18 protein, the nematode will appear dpy. If the inhibitor is non-specific and knocks out both P4H genes, the progeny of the tested animal will have a lethal phenotype.

In another embodiment, one would examine the nematodes for the P4H activity level (preferably the P4H:proline ratio). A reduced P4H activity would indicate that the compound is an inhibitor.

In another embodiment of the invention, one could compare the amount of inhibitor needed to affect wild-type, dpy-18 or psy-2 mutants. Dpy-18 and psy-2 mutations will be more sensitive to inhibitor.

Worms with a dpy phenotype appear to be shorter in length (approximately two/thirds wild-type) when viewed with a dissecting microscope. Worms with a lethal phenotype appear to be dead embryos when viewed with a dissecting microscope.

Activators of prolyl-4-hydroxylase will rescue the dpy-18 or phy-1 phenotype. Potentially, phy-1 or dpy-18 nematodes could be exposed to the test compounds and any redundant expression could be activated to rescue the mutant phenotype.

The Examples below and Friedman, et al., 2000, describe how to create suitable mutants in *C. elegans*. Preferably, the nematode will be one of the genus Caenorhabditis, preferably *C. briggsae*. If one wished to use another nematode, such as *C. briggsae*, one of skill in the art would be able to create analogous mutants using the presented information.

EXAMPLES

Experimental Procedures

Worm Strains

All wild-type *C. elegans* were from an N2 Bristol strain. Worms were cultured at 20° C. under standard conditions unless otherwise noted (J. E. Sulston and J. Hodgkin, *Methods. In The Nematode Caenorhabditis elegans*, pp. 587–606, 1988). LG II:unc-4(e120) was used as a marker for transgenic assays. LG III:dpy-18(ok162) is a deletion mutation isolated specifically as a knock-out of the prolyl 4-hydroxylase on chromosome III. We found that dpy-18 phenotype corresponds to the absence of prolyl 4-hydroxylase. 11 alleles (mutations in the dpy-18 gene) are known—dpy-18: e346, e364, e499, e1096, e1270, e1862, h662, s361, s1304, s1305, s1306. LG IV:unc-22(e66) is a mutation that can be used to recognize chromosome IV, and poh-1(ok-177) is a deletion mutation isolated specifically as a knock-out of the prolyl 4-hydroxylase gene on chromosome IV.

hT2(I:III) is a rearrangement that contains a mutation in the dpy-18 gene. Thus, Ht2(I:III) has a dpy phenotype and is not complemented by dpy-18 mutations.

Description of Prolyl 4-hydroxylase Genes in *C. elegans*

Our searches using FASTA and BLAST with the human prolyl 4-hydroxylase sequence against the *C. elegans* genome revealed the presence of two *C. elegans* genes with homology to prolyl 4-hydroxylase. Y47D3B.10 is the transcript which corresponds to the prolyl 4-hydroxylase on LGIII (which we have determined to correspond to the dpy-18 gene) and F35G2.4 is the transcript which corresponds to the prolyl 4-hydroxylase on LGIV. Phylogenetic analysis of the two genes compared with that of alpha I and alpha II of human, mouse, rat, chicken, drosophila and a virus prolyl 4-hydroxylase using the programs PILEUP of GCG and PAUP suggest that the two genes are more closely related to each other than to any other sequences.

Isolation of Deletion Mutants

To induce deletion mutations in the two different prolyl 4-hydroxylase genes in *C. elegans* we sent the following primers to Robert Barstead and Gary Moulder at the Oklahoma Medical Research Foundation. These researchers provide a service to the *C. elegans* community by isolating deletions in PCR screens of mutagenized populations. L4 hermaphrodites were treated with trimethylpsoralen and UV light as described (see *http://snmc01.omrf.uokhsc.edu/revgen/RevGen.html* and Dernburg, et al., *Cell* 94(3): 387–398, 1998, for a protocol).

Offspring from mutagenized animals were cultured in groups of 500. After one generation genomic DNA was prepared from pools of worms, and nested primers were used in two successive rounds of PCR. The external primers for Y47D3B.10 (corresponding to dpy-18) were CACGAC-GAGGAAGAGCGACTG (SEQ ID NO:1) and TAC-GATTTCCAGTTCCCAAGC (SEQ ID NO:2): the internal primers were GAAGAAGCTGTCGGAGGAGTA (SEQ ID NO:3) and ACGGCTAGTGGGTTGAATCTC (SEQ ID NO:4). The expected product from amplification of wild-type genomic DNA is 3.2 kb. The external primers for F35G2.4 (corresponding to poh-1) were GCTCATGCA-GATTTGTTCACT (SEQ ID NO:5) and GTCAGCAG-GAAGGCAGTAAAC (SEQ ID NO:6); the internal primers were GAGCAGAGAAGGATGTAACAA (SEQ ID NO:7) and ATAGTGCGCATTTCCGTTTCA (SEQ ID NO:8). The expected product from amplification of wild-type genomic DNA is 2.8 kb.

Analysis of Hydroxylated Proline:Proline in Worm Cuticles

As a measure of prolyl 4-hydroxylase activity, the ratio of 4-hydroxyproline:proline was determined in the highly collagenous worm cuticle.

Isolation of Cuticles

To isolate cuticles, worms were bleached and embryos were collected and washed extensively in M9. Embryos were allowed to hatch overnight in M9 and then collected and washed and plated and allowed to grow to L4. L4 worms were collected and washed in M9 and frozen at −80° C. 2 ml of packed worms were defrosted and washed with sonication buffer.

Cuticle isolation was performed as a modification of Edgar, et al., 1981. Nematodes were suspended in 3 ml of sonication buffer (10 mM Tris-HCl, pH 7.4, 1 mM EDTA, 1 mM phenylmethanesulfonyl fluoride [PMSF], and given ten 20 second bursts of a Branson Sonifier 450 at 50% Duty Cycle and 5–7 output control. Cuticle pieces were collected by centrifugation for 4 minutes at 2000×rpm in a Sorvall Super T21 and washed several times with 10 ml sonication buffer. Cuticles were then transferred to a 1.5 ml microfuge tube, suspended in 1 ml of ST buffer (1% SDS, 0.125 M Tris-HCl, pH 6.8) and heated for 2 minutes in a boiling water bath. The sample was then incubated for 6 hours, spun down for 60 seconds in an Eppendorf microcentrifuge, extracted again with ST buffer as described and left shaking overnight. The disulfide cross-linked proteins of the cuticle were solubilized by heating purified cuticles for 2 minutes in a boiling water bath in 0.5 ml of ST buffer with 5% β-mercaptoethanol (BME). The sample was rocked for 6 hours on a platform shaker and the solution was extracted and the sample was treated for a second time and left to rock overnight. The insoluble cuticle material was washed several times with distilled water and speed vac dried. All protein samples were stored at −20° C.

Samples for amino acid analysis were hydrolyzed in 6N HCl/0.1% phenol at 110° C. for 22 hours and assayed for the ratio of 4-hydroxyproline:proline at MIT's Biopolymer laboratory (Cambridge, Mass.).

Phenotypes

After receiving deletion mutants in the two prolyl 4-hydroxylase genes we analyzed the phenotypes of the individual mutants and the double mutants.

The fact that the dpy phenotype corresponds to the prolyl 4-hydroxylase on LGIII provides an easy method of assaying loss of function of this gene. If one knocks out dpy-18, one gets a short, fat, little worm, hence the name "dpy" for dumpy. The phy-2 gene is wild type at 20° C. but is more sensitive to inhibitor concentration than is the wild-type worm, thus allowing one to identify the specific knock-out of this gene.

The double mutant phenotype dpy-18;phy-2 is an extremely embryonic lethal animals allowing us to look for inhibitors of both genes or all prolyl 4-hydroxylases.

RNAi:

Double-stranded RNA was produced using PCR-generated fragments of phy-1 and dpy-18 cDNA with T7 promoters linked to primers specific to said DNA. The RNA was then produced using the T7 MegaScript RNA kit (Ambion). The RNA was injected at 5 mg/ml into N2 animals individually and in combination. The worms were grown at 15° C., 20° C. and 25° C. RNA interference technology may be used to create the same knock-out phenotypes as those seen by the deletion mutations.

Proposed Isolation of the Human Prolyl 4-hydroxylase Alpha I and Alpha II Subunit cDNAs.

Below we describe a proposed method of isolating human P4H gene. One of skill in the art would be aware of modifications and alternative methods that would be equally suitable.

The two full-length human prolyl 4-hydroxylase mRNAs have been described in Helaakoski. et al. 1994 (T. Helaakoski, et al., *J. Biol. Chem.* 269(45):27847–54, 1994) and Annunen, et al., 1997 (P. Annunen, et al.,*J. Biol. Chem.* 272(28):17342–8, 1997.) respectively. Using the sequences described in the above mentioned papers Genebank ACCESSION # M24486, and M24487 corresponding to the two alpha I subunits and ACCESSION # U90441 corresponding to the alpha II subunit one could use the standard BLAST program and search the Genbank database for IMAGE consortium clones.

If one cannot obtain a full length clone from the IMAGE consortium one could use standard methods such as RT-PCR to create a full-length cDNA from human RNA or a human cDNA library.

Small Molecule Inhibition of Prolyl 4-Hydroxylase Activity

Small molecules that inhibit protein function can be used to confirm and extend results from genetic experiments. We tested two known prolyl 4-hydroxylase inhibitors for their effects on *C. elegans*. FIG. 1 shows the structures of these inhibitors: 2,4-diethylpyridine dicarboxylate and dimethyloxalylglycine (Inhibitor I and Inhibitor II, respectively). Both inhibitors limit prolyl 4-hydroxylase activity in cells, where their esters are hydrolyzed to form competitors of α-ketoglutarate. We also tested Inhibitor III (which is similar in structure to Inhibitor II) and Inhibitor IV (which is similar in structure to Inhibitor I). Neither Inhibitor III nor Inhibitor II is known to limit prolyl 4-hydroxylase activity in cells.

Figure 2A:
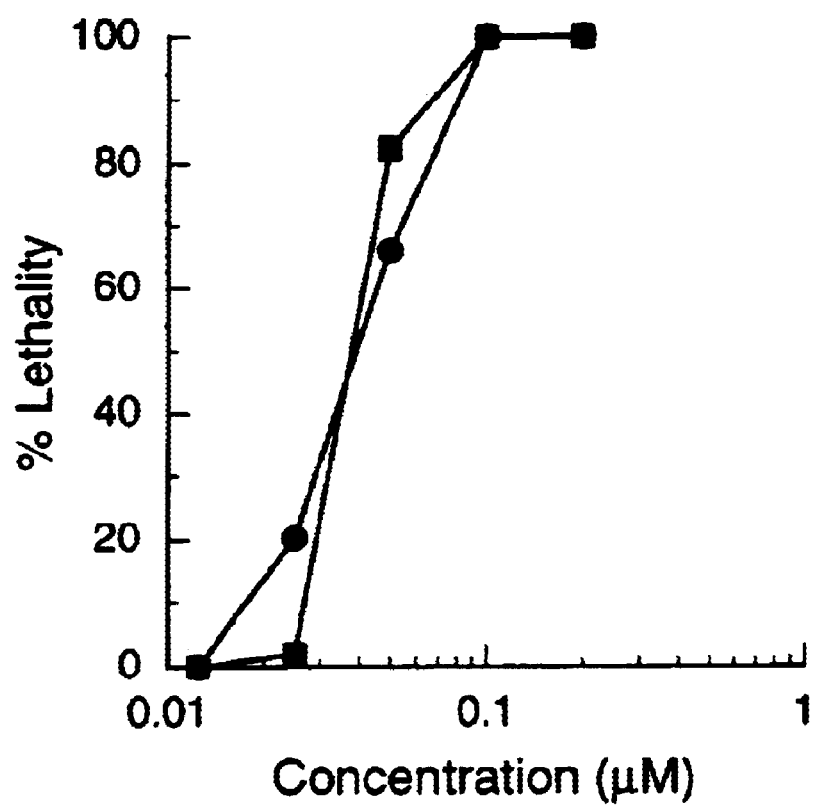
FIG. 2A and FIG. 2B graphs percent lethality versus concentration of P4H inhibitors. Inhibitor I is depicted in FIG. 2A and Inhibitor II is depicted in FIG. 2B.
Figure 2B:
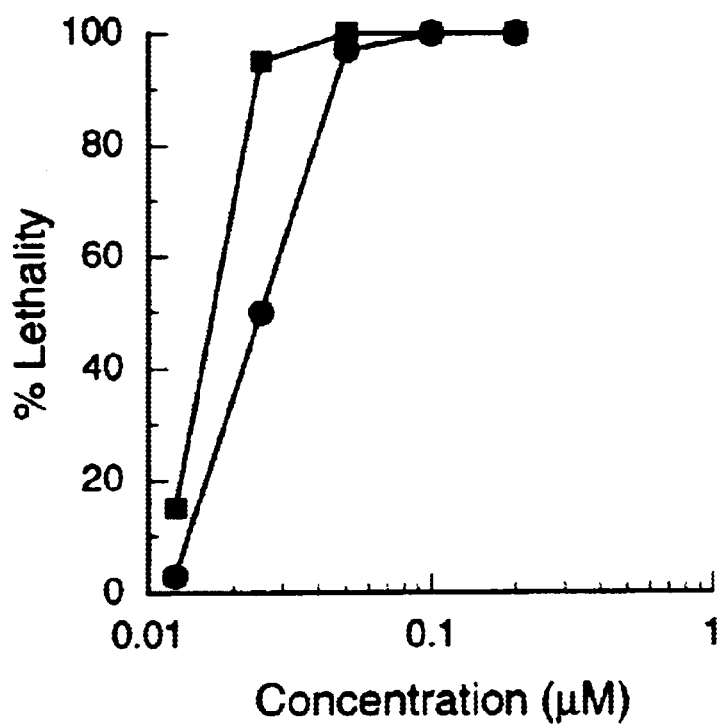

We exposed adult hermaphrodites that were genotypically wild-type, dpy-18(ok162) or phy-2(ok177) to varying concentrations of inhibitors. The animal placed in inhibitor was apparently unaffected, but dramatic effects were observed among their progeny. Indeed, when exposed to a high level of Inhibitor I or II (2.7 $\mu$M and 1.3 $\mu$M, respectively), all progeny died, regardless of genotype (FIGS. 2A and 2B). The dead embryos arrested at the two-fold stage and then exploded; a phenotype reminiscent of the dpy-18; phy-2 dead embryos. This suggests that exposure to the inhibitors results in a lowered prolyl 4-hydroxylase activity.

At a 10-fold lower concentration, the inhibitors affected dpy-18(ok162), but not phy-2(ok177) progeny. To ask whether animals with a Dpy phenotype were unusually sensitive to inhibitor, we tested dpy-10(e128), dpy-11(e224), dpy-13(e184), dpy-17(e364) and dpy-20(e1282) mutants for inhibitors effects. However, these other dpy mutants were comparable to wild-type animals in their response to both inhibitors. Therefore, the sensitivity of dpy-18 mutants to inhibitors is not caused by its Dpy phenotype. In dpy-18 mutants, the only prolyl 4-hydroxylase activity remaining is PHY-2, and conversely, in phy-2 mutants, the only remaining activity is DPY-18. We suggest that the effect of the inhibitor on dpy-18 mutants reflects inhibition of the remaining PHY-2, and vice versa. Because dpy-18, but not phy-2, progeny were affected by inhibitor at low concentration, we suggest that PHY-2 is either less abundant or more sensitive than DPY-18.

Both Inhibitor III (at $\leq$29 $\mu$M) and Inhibitor IV ($\leq$3.2 mM) had no effect on the viability of dpy-18 worms. (See FIG. 1 for structure of Inhibitors III and IV.) These two molecules had not been described previously as inhibitors of P4H.

---

We claim:

1. A method for evaluating a test compound's ability to inhibit prolyl-4-hydroxylase (P4H), comprising the steps of:
   (a) introducing a test compound into a test chimeric *Caenorhabditis elegans*, a P4H-gene modified *Caenorhabditis elegans*, or a wild-type *Caenorhabditis elegans*, wherein the test chimeric *Caenorhabditis elegans* comprises a P4H gene that complements an endogenous P4H gene mutation, wherein the mutation results in an endogenous P4H that is not functional, and
   (b) observing the effect of the test compound on the prolyl 4-hydroxylase activity of the progeny of the test nematode, P4H-gene modified nematode or the wild-type nematode and determining that the effect of the test compound is due to its effect on prolyl-4-hydroxylase activity, wherein a dpy or embryonic lethal phenotype indicates prolyl-4-hydroxylase inhibition.

2. The method of claim 1, wherein the test compound is a chemical.

3. The method of claim 1, wherein the test compound is a protein or peptide.

4. The method of claim 1, wherein the introduction of the test compound involves placing the nematode in a solution containing the test compound.

5. The method of claim 1, wherein the test compound is introduced into a wild-type nematode and the observation of dpy or embryonic lethal phenotype indicates nematode prolyl 4-hydroxylase inhibition.

6. The method of claim 1, wherein the test compound is introduced into a P4H-gene modified nematode and the observation of a dpy or embryonic lethal phenotype indicates P4H inhibition.

7. The method of claim 1, wherein the introduction of a test compound is into a test chimeric nematode and the observation of dpy or embryonic lethal phenotype indicates non-native prolyl 4-hydroxylase inhibition.

8. The method of claim 1, wherein the test chimeric *Caenorhabditis elegans* harbors a dpy-18 mutation.

9. The method of claim 1 wherein the test compound is part of a combinatorial chemical library.

10. A method for evaluating a test compound's ability to increase prolyl 4-hydroxylase, comprising the step of:
    (a) introducing a test compound into a *Caenorhabditis elegans* comprising a dpy-18 or phy-1 mutation phenotype, and
    (b) observing the effect of the test compound on the progeny of the *Caenorhabditis elegans* and determining that the effect of the test compound is due to its effect on prolyl-4-hydroxylase activity, wherein the rescue of the dpy-18 or phy-1 phenotype indicates an increased level of prolyl-4-hydroxylase activity.

11. The method of claim 10 wherein the test compound is part of a combinatorial library.

12. A method for evaluating a test compound's ability to inhibit P4H, comprising the steps of:
    (a) introducing a test compound into a test chimeric *Caenorhabditis elegans*, a P4H-gene modified *Caenorhabditis elegans*, or a wild-type *Caenorhabditis elegans*, wherein the test chimeric *Caenorhabditis elegans* has a complemented P4H gene mutation and wherein the mutation results in a non-functional endogenous P4H, and
    (b) measuring the level of P4H activity of the progeny of the test *Caenorhabditis elegans*, P4H gene modified *Caenorhabditis elegans* or wild-type *Caenorhabditis elegans* and determining that the effect of the test compound is due to its effect on prolyl-4-hydroxylase activity, wherein a lower P4H activity compared to untested control *Caenorhabditis elegans* indicates that the test compound is an inhibitor of P4H.

13. The method of claim 12 wherein the measurement of P4H activity is via determining a ratio of P4H to proline.

14. The method of claim 12 wherein the test compound is part of a combinatorial library.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 1
cacgacgagg aagagcgact g                                              21

<210> SEQ ID NO 2
<211> LENGTH: 21
<212> TYPE: DNA
```

```
<213> ORGANISM: Artificial Sequence
<220> FEATURE:
<223> OTHER INFORMATION: Description of Artificial Sequence:PCR Primer

<400> SEQUENCE: 2
tacgatttcc agttcccaag c                                          21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 3
gaagaagctg tcggaggagt a                                          21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 4
acggctagtg ggttgaatct c                                          21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 5
gctcatgcag atttgttcac t                                          21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 6
gtcagcagga aggcagtaaa c                                          21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:PCR Primer

<400> SEQUENCE: 7
gagcagagaa ggatgtaaca a                                          21

<210> SEQ ID NO 8
<211> LENGTH: 21
<212> TYPE: DNA
<213> ORGANISM: Artificial Sequence
```

```
<220> FEATURE:
<223> OTHER INFORMATION: Description of Artificial Sequence:PCR Primer

<400> SEQUENCE: 8
atagtgcgca tttccgtttc a                                                    21
```